(12) United States Patent
Diaz et al.

(10) Patent No.: US 6,991,641 B2
(45) Date of Patent: Jan. 31, 2006

(54) LOW PROFILE VASCULAR FILTER SYSTEM

(75) Inventors: Pedro Diaz, Pembroke Pines, FL (US); Jay S. Yadav, Hunting Valley, OH (US)

(73) Assignee: Cordis Corporation, Miami Lakes, FL (US)

( * ) Notice: Subject to any disclaimer, the term of this patent is extended or adjusted under 35 U.S.C. 154(b) by 372 days.

(21) Appl. No.: 10/095,925

(22) Filed: Mar. 12, 2002

(65) Prior Publication Data

US 2002/0103501 A1   Aug. 1, 2002

Related U.S. Application Data

(63) Continuation-in-part of application No. 09/249,377, filed on Feb. 12, 1999, now Pat. No. 6,391,044.

(51) Int. Cl.
*A61B 17/22* (2006.01)

(52) U.S. Cl. ...................................... 606/200
(58) Field of Classification Search ................. 606/200
See application file for complete search history.

(56) References Cited

U.S. PATENT DOCUMENTS

| | | |
|---|---|---|
| 3,435,824 A | 4/1969 | Gamponia |
| 3,889,685 A | 6/1975 | Miller, Jr. et al. |
| 3,952,747 A | 4/1976 | Kimmell, Jr. |
| 4,230,119 A | 10/1980 | Blum |
| 4,349,029 A | 9/1982 | Mott |
| 4,425,908 A | 1/1984 | Simon |
| 4,494,531 A | 1/1985 | Gianturco |
| 4,545,390 A | 10/1985 | Leary |
| 4,619,246 A | 10/1986 | Molgaard-Nielsen et al. |
| 4,619,274 A | 10/1986 | Morrison |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,793,348 A | 12/1988 | Palmaz |
| 4,794,928 A | 1/1989 | Kletschka |
| 4,832,055 A | 5/1989 | Palestrant |
| 4,842,579 A | 6/1989 | Shiber |

(Continued)

FOREIGN PATENT DOCUMENTS

EP      0 737450 A1    10/1996

(Continued)

OTHER PUBLICATIONS

A. Cragg et al., A New Percutaneous Vena Cava Filter, AJR, 141, Sep. 1983, pp. 601-604.

(Continued)

Primary Examiner—Michael Thaler

(57) ABSTRACT

A removable, low profile, vascular filter system for capture and retrieval of emboli while allowing continuous perfusion of blood, comprising a guidewire having proximal and distal markers, a filter delivery and deployment system, having an outer member and an inner member, and a filter removably attached near the distal end of the inner member. The filter comprises proximal and distal basket sleeves which position the filter between the proximal and distal markers on the guidewire, after the guidewire is in position past the vessel occlusion. The guidewire placement prior to filter delivery may facilitate access to the interventional site, especially through tortuous anatomy. Also, retrievability of the filter from the wire may avoid loss of guidewire position, which may occur following removal of filters permanently attached to guidewires.

16 Claims, 3 Drawing Sheets

U.S. PATENT DOCUMENTS

| | | |
|---|---|---|
| 4,873,978 A | 10/1989 | Ginsburg |
| 4,884,573 A | 12/1989 | Wajay et al. |
| 4,921,484 A | 5/1990 | Hillstead |
| 4,926,858 A | 5/1990 | Gifford, III et al. |
| 4,957,501 A | 9/1990 | Lahille et al. |
| 4,969,891 A | 11/1990 | Gewertz |
| 4,990,156 A | 2/1991 | Lefebvre |
| 5,011,488 A | 4/1991 | Ginsburg |
| 5,053,008 A | 10/1991 | Bajaj |
| 5,059,205 A | 10/1991 | El-Nounou et al. |
| 5,092,839 A | 3/1992 | Kipperman |
| 5,095,915 A | 3/1992 | Engelson |
| 5,108,419 A | 4/1992 | Reger et al. |
| 5,133,733 A | 7/1992 | Rasmussen et al. |
| 5,152,777 A | 10/1992 | Goldberg et al. |
| 5,190,540 A | 3/1993 | Lee |
| 5,190,546 A | 3/1993 | Jervis |
| 5,201,757 A | 4/1993 | Heyn et al. |
| 5,242,462 A | 9/1993 | El-Nounou et al. |
| 5,279,546 A | 1/1994 | Mische et al. |
| 5,324,304 A | 6/1994 | Rasmussen |
| 5,329,942 A | 7/1994 | Gunther et al. |
| 5,413,586 A | 5/1995 | Dibie et al. |
| 5,421,832 A | 6/1995 | Lefebvre |
| 5,496,277 A | 3/1996 | Termin et al. |
| 5,531,788 A | 7/1996 | Dibie et al. |
| 5,549,626 A | 8/1996 | Miller et al. |
| 5,632,760 A | 5/1997 | Sheiban et al. |
| 5,662,631 A | 9/1997 | Marx |
| 5,662,671 A | 9/1997 | Barbut et al. |
| 5,681,347 A | 10/1997 | Cathcart et al. |
| 5,695,519 A | 12/1997 | Summers et al. |
| 5,709,704 A | 1/1998 | Nott et al. |
| 5,749,890 A | 5/1998 | Shaknovich |
| 5,769,816 A | 6/1998 | Barbut et al. |
| 5,779,716 A | 7/1998 | Cano et al. |
| 5,807,398 A | 9/1998 | Shaknovich |
| 5,810,874 A | 9/1998 | Lefebvre |
| 5,814,064 A | 9/1998 | Daniel et al. |
| 5,827,324 A | 10/1998 | Cassell et al. |
| 5,836,969 A | 11/1998 | Kim et al. |
| 5,848,964 A | 12/1998 | Samuels |
| 5,876,367 A | 3/1999 | Kaganov et al. |
| 5,902,263 A | 5/1999 | Patterson et al. |
| 5,910,154 A | 6/1999 | Tsugita et al. |
| 6,001,118 A | 12/1999 | Daniel et al. |
| 6,013,093 A | 1/2000 | Nott et al. |
| 6,051,014 A | 4/2000 | Jang |
| 6,053,932 A | 4/2000 | Daniel et al. |
| 6,059,814 A | 5/2000 | Ladd |
| 6,059,825 A | 5/2000 | Hobbs et al. |
| 6,074,357 A | 6/2000 | Kaganov et al. |
| 6,080,178 A | 6/2000 | Meglin |
| 6,126,673 A | 10/2000 | Kim et al. |
| 6,152,946 A | 11/2000 | Broome et al. |
| 6,165,179 A | 12/2000 | Cathcart et al. |
| 6,165,200 A | 12/2000 | Tsugita et al. |
| 6,168,604 B1 | 1/2001 | Cano |
| 6,179,859 B1 | 1/2001 | Bates et al. |
| 6,179,861 B1 | 1/2001 | Khosravi et al. |
| 6,187,015 B1 | 2/2001 | Brenneman |
| 6,203,561 B1 | 3/2001 | Ramee et al. |
| 6,214,025 B1 | 4/2001 | Thistle et al. |
| 6,221,096 B1 | 4/2001 | Aiba et al. |
| 6,241,746 B1 | 6/2001 | Bosma et al. |
| 6,258,115 B1 | 7/2001 | Dubrul |
| 6,267,776 B1 | 7/2001 | O'Connell |
| 6,267,777 B1 | 7/2001 | Bosma et al. |
| 6,270,513 B1 | 8/2001 | Tsugita et al. |
| 6,273,900 B1 | 8/2001 | Nott et al. |
| 6,277,138 B1 | 8/2001 | Levinson et al. |
| 6,290,710 B1 | 9/2001 | Cryer et al. |
| 6,336,934 B1 | 1/2002 | Gilson et al. |
| 6,346,116 B1 | 2/2002 | Brooks et al. |

FOREIGN PATENT DOCUMENTS

| | | |
|---|---|---|
| EP | 0 791 340 A1 | 8/1997 |
| FR | 2 652 267 A1 | 3/1991 |
| FR | 2 606 642 A1 | 5/1998 |
| GB | 2020557 A1 | 11/1978 |
| SU | 764684 A1 | 9/1980 |
| WO | WO 96/01591 A1 | 1/1996 |

OTHER PUBLICATIONS

A. Cragg et al., Nonsurgical Placement of Arterial Endoprosthesis; A New Technique Using Nitinol Wire, AJR, Apr. 1983, p. 261-263.

Eichelter, et al., Prophylaxis of Pulmonary Embolism, Archives of Surgery, vol. 97, Aug. 1968, p. 348 et seq.

G.Lund et al., Long-Term Patency of the Ductus Arteriosus After Balloon Dilatation: An Experimental Study, AJR, Sep. 1983, p. 772.

Greenfield, et al., A New Intercaval Filter Permitting Continued Flow and Resolution of Emboli, Surgery, vol. 73, No. 4, pp. 599-606.

M. H. Wholey et al, PTA and Stents in the Treatment of Extraclavical Circulation, Journal of Advanced Cardiology vol. 9 Suppl. E. 1996, pp. 25E-30E.

Topol, Eric J., et al. Recognition of the Importance of Embolization in Atherosclerotic Vascular Disease American Heart Journal 2000.

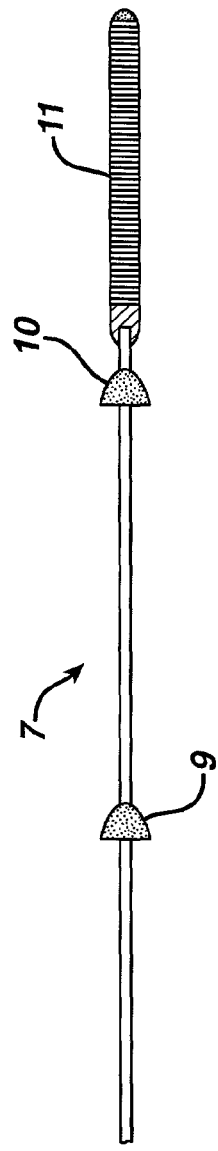
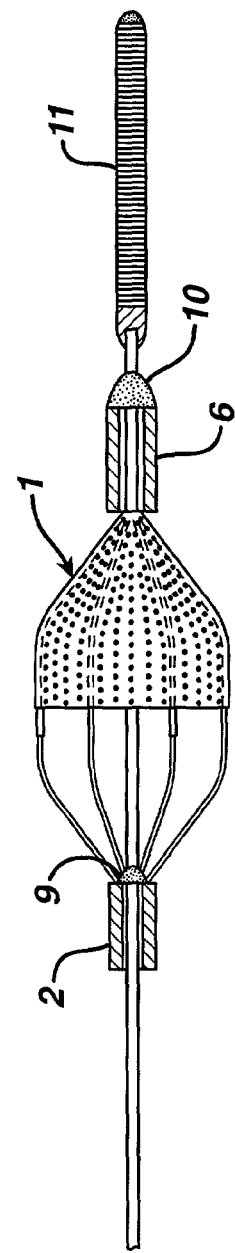
FIG. 3
FIG. 4

LOW PROFILE VASCULAR FILTER SYSTEM

CROSS-REFERENCE TO RELATED APPLICATIONS

This application is a Continuation-in-Part application of U.S. patent application Ser. No. 09/249,377 now U.S. Pat. No. 6,391,044 filed Feb. 12, 1999.

BACKGROUND OF THE INVENTION

I. Field of the Invention

The present invention relates to the treatment of vascular disease, and more particularly to a vascular filter system for use during medical procedures.

II. Discussion of the Related Art

Percutaneous transluminal coronary angioplasty (PTCA), stenting and atherectomy are therapeutic medical procedures used to increase blood flow through the coronary arteries. These procedures may often be performed as alternatives to coronary bypass surgery. Percutaneous transluminal angioplasty (PTA) and stenting may often be performed as alternatives to carotid endarterectomy, and femoral-popliteal bypass procedures. In PTCA or PTA procedures, the angioplasty balloon is inflated within the stenosed vessel, at the location of an occlusion, in order to shear and disrupt the wall components of the vessel to obtain an enlarged lumen. In stenting, an endoluminal prosthesis is implanted in the vessel to maintain patency following the procedure. In atherectomy, a rotating blade is used to shear plaque from the arterial wall.

One of the potential complications associated with all these techniques is the accidental dislodgment of plaque, thrombus or other embolic particulates generated during manipulation of the vessel, thereby potentially causing occlusion of the narrower vessels downstream and ischemia or infarct of the organ which the vessel supplies. Such emboli may be extremely dangerous to the patient, and may result in myocardial infarction, stroke or limb ischemia. In 1995, Waksman et al. disclosed that distal embolization is common after directional atherectomy in coronary arteries and saphenous vein grafts. See Waksman et al., American Heart Journal 129(3): 430–5 (1995). This study found that distal embolization occurs in twenty-eight percent (31 out of 111) of the patients undergoing atherectomy. In January 1999, Jordan, Jr. et al. disclosed that treatment of carotid stenosis using a percutaneous angioplasty with stenting procedure is associated with more than eight times the rate of microemboli seen using carotid endarterectomy. See Jordan, Jr. et al., Cardiovascular Surgery 7(1): 33–8 (1999). Microemboli, as detected by transcranial Doppler monitoring in this study, have been shown to be a potential cause of stroke. The embolic materials include calcium, intimal debris, atheromatous plaque, and thrombi.

In order to initiate these procedures, one must first introduce a guidewire into the lumen of the vessel to serve as a conduit for other interventional devices, such as angioplasty balloons and stent delivery systems. This guidewire must be advanced into a position past the location of the occlusion. Guidewires must be capable of traversing tortuous pathways within the body, consisting of bends, loops and branches. For this reason, guidewires need to be flexible, but they should also be sufficiently stiff to serve as conduits for other devices. In addition, they must be "torqueable" to facilitate directional changes as they are guided into position.

Guidewires are well known in the art, and are typically made of stainless steel, tantalum or other suitable materials, in a variety of different designs. For example, U.S. Pat. Nos. 4,545,390 and 4,619,274 disclose guidewires in which the distal segment is tapered for greater flexibility. The tapered section may be enclosed in a wire coil, typically a platinum coil, which provides increased column strength and torqueability. Another design is identified in U.S. Pat. No. 5,095,915, where the distal segment is encased in a polymer sleeve with axially spaced grooves to provide bending flexibility.

Vascular filters are also well known in the art, especially vena cava filters, as disclosed in U.S. Pat. Nos. 4,727,873 and 4,688,553. There is also a substantial amount of medical literature describing various designs of vascular filters and reporting the results of clinical and experimental use thereof. See, for example, the article by Eichelter and Schenk, entitled "Prophylaxis of Pulmonary Embolism," Archives of Surgery, Vol. 97 (August, 1968). See, also, the article by Greenfield, et al., entitled "A New Intracaval Filter Permitting Continued Flow and Resolution of Emboli", Surgery, Vol. 73, No. 4 (1973).

Vascular filters are often used during a postoperative period, when there is a perceived risk of a patient encountering pulmonary embolism resulting from clots generated peri-operatively. Pulmonary embolism is a serious and potentially fatal condition that occurs when these clots travel to the lungs. The filter is therefore typically placed in the vena cava to catch and trap clots before they can reach the lungs.

Many of the prior art vascular filters are intended to be permanently placed in the venous system of the patient, so that even after the need for the filter has passed, the filter remains in place for the life of the patient. U.S. Pat. No. 3,952,747 discloses a stainless steel filtering device that is permanently implanted transvenously within the inferior vena cava. This device is intended to treat recurrent pulmonary embolism. Permanent implantation is often deemed medically undesirable, but it is done because filters are implanted in patients in response to potentially life-threatening situations.

To avoid permanent implantation where possible, it is highly desirable to provide an apparatus and method for preventing embolization associated with angioplasty, stenting or other procedures. In particular, it is desirable to provide a device which may be temporarily placed within the vascular system to collect and retrieve plaque, thrombus and other embolic particulates which have been dislodged during angioplasty, stenting or other procedures. Such a device is removed at the end of the procedure. U.S. Pat. Nos. 6,179,861 and 6,001,118 disclose guidewire-based filters where the filter resembles a windsock and is supported by one or more articulated support hoops. U.S. Pat. Nos. 5,814,064 and 5,827,324 disclose guidewire-based filter devices, wherein the filter is expanded to a predetermined diameter through the introduction of a fluid or a gas. U.S. Pat. Nos. 6,168,604 and 6,152,946 disclose guidewire-based filters, wherein the diameter of the filter is controlled by advancing and retracting a sheath over the filter component.

One concern commonly encountered with these devices is that the filter is attached to the guidewire, which increases the profile or diameter thereof, making it is difficult to push and track these devices through the vasculature, to reach the treatment site. A related concern commonly encountered with these devices is that if the filter becomes clogged with emboli, such that distal perfusion is no longer possible, the filter must be removed and replaced, thereby losing guidewire position.

The prior art fails to disclose any guidewire-based vascular filters which may be used to address the clinical problems of poor pushability and trackability through the vasculature, and loss of guidewire position upon removal of filters permanently attached to guidewires.

SUMMARY OF THE INVENTION

The present invention provides a vascular filter system which may be used to address the clinical problems of poor pushability and trackability through the vasculature, and loss of guidewire position upon removal of filters permanently attached to guidewires, as briefly described above.

An objective of the present invention is to provide a vascular filter which is positioned on a guidewire after the distal end of the guidewire has crossed the lesion and is in position past an occlusion in a lumen of a vessel. Therefore, the present invention enables the physician to successfully reach the treatment site with a low profile device. Then, the present invention provides a filter to capture embolic particulates that may be released during the procedure, while also allowing perfusion of distal vessels. A further objective of the present invention is to provide a vascular filter that is retrievable while maintaining guidewire position.

The filter system of the present invention comprises a guidewire having proximal and distal markers; a filter deployment and delivery system comprising an inner member and an outer member, with a filter removably attached near the distal end of the inner member; proximal and distal basket sleeves attached near the proximal and distal ends of the filter; and a retrieval catheter coaxially disposable around the guidewire and the filter. The low profile guidewire of the present invention, comprising proximal and distal markers near its distal end, but without an attached filter, is used to access the interventional site. If the anatomy is tortuous, such that access would be difficult if not impossible with a filter attached, access may still be achieved with this low profile guidewire. Then, the filter deployment and delivery system of the present invention, comprising an inner member and an outer member, is introduced, with the filter removably attached to the inner member of the filter deployment and delivery system. The outer member collapses and constrains the filter, allowing it to achieve a smaller first diameter. The filter of the present invention comprises proximal and distal basket sleeves. The distal basket sleeve is sized to successfully ride over the proximal marker on the guidewire, but not the distal marker, so the filter is positioned between these two markers. Then, the outer member of the filter deployment and delivery system is retracted to deliver the filter. The inner member is then withdrawn, and the filter remains positioned on the guidewire, between the proximal and distal markers. The filter captures embolic particulates during the procedure. The retrieval catheter is then employed to retrieve the filter and the guidewire, if the procedure is complete. If the procedure is incomplete, but the filter is full and is prohibiting distal perfusion, the filter alone may be removed, so that guidewire position is not lost, and the remainder of the procedure may be completed.

In accordance with one aspect, the present invention is directed to a low profile vascular filter system comprising a guidewire having proximal and distal markers. The low profile vascular filter system further comprises a filter deployment and delivery system coaxially disposed around the guidewire, with the filter deployment and delivery system comprising an inner member and an outer member, a filter removably attached near the distal end of the inner member, and proximal and distal basket sleeves attached near the proximal and distal ends of the filter. The low profile vascular filter system further comprises a retrieval catheter coaxially disposable around the guidewire and the filter. The retrieval catheter is used to collapse the filter, and to remove the filter and the guidewire from the lumen of the vessel.

In accordance with another aspect, the present invention is directed to a low profile vascular filter system comprising a guidewire having proximal and distal markers. The low profile vascular filter system further comprises a filter deployment and delivery system coaxially disposed around the guidewire, with the filter deployment and delivery system comprising an inner member and an outer member, a filter removably attached near the distal end of the inner member, and proximal and distal basket sleeves attached near the proximal and distal ends of the filter. The low profile vascular filter system further comprises a retrieval catheter coaxially disposable around the guidewire and the filter. The retrieval catheter is used to collapse the filter, to remove the filter from the guidewire, and to withdraw the filter from the lumen of the vessel. The guidewire position is thus maintained, to complete the interventional procedure.

An advantage of the present invention is that the filter is delivered to the guidewire after the low profile guidewire has been used to gain access to the interventional site, thereby facilitating access to the site through tortuous anatomy. Another advantage of the present invention is that a full filter may be collapsed and retrieved without removing the guidewire, thereby allowing the operator to maintain guidewire position if the interventional procedure is incomplete.

BRIEF DESCRIPTION OF THE DRAWINGS

The present invention will be apparent upon consideration of the following detailed description, taken in conjunction with the accompanying drawings, in which the reference characters refer to like parts throughout, and in which:

FIG. 3 illustrates an enlarged, partial, cross-sectional view of an exemplary embodiment of the guidewire of the low profile vascular filter system, in accordance with the present invention.

FIG. 4 illustrates an enlarged, partial, cross-sectional view of an exemplary embodiment of the filter and guidewire of the low profile vascular filter system, with the filter in the open position, in accordance with the present invention.

DETAILED DESCRIPTION OF THE PREFERRED EMBODIMENTS

The present invention relates to a low profile vascular filter system for use in percutaneous angioplasty and stenting, and substantially reduces the risk of distal embolization during interventional procedures. The low profile vascular filter system is designed to address the clinical problems of poor pushability and trackability through the vasculature, and loss of guidewire position upon removal of guidewire-based filters. The low profile vascular filter system comprises a guidewire having proximal and distal markers, and a filter deployment and delivery system coaxially disposed around the guidewire. The filter deployment and delivery system comprises an inner member and an outer member, with a filter removably attached near the distal end of the inner member, and proximal and distal basket sleeves attached near the proximal and distal ends of the filter. The low profile vascular system also comprises a retrieval catheter coaxially disposable around the guidewire and the filter.

Figure 1:
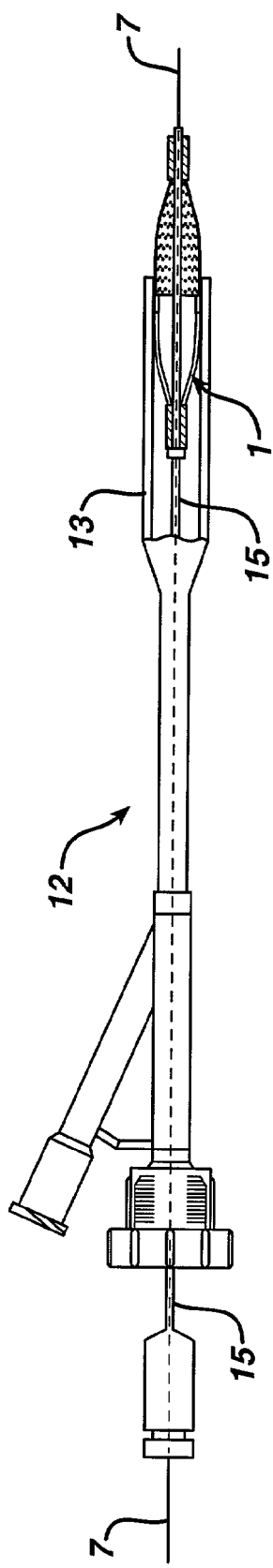
FIG. 1 illustrates an enlarged, cross-sectional view of an exemplary embodiment of the low profile vascular filter system, with the filter in the collapsed position, in accordance with the present invention.

FIG. 1 illustrates an exemplary embodiment of the low profile vascular filter system in accordance with the present invention. In this exemplary embodiment, the low profile vascular filter system comprises a guidewire 7, and a filter deployment and delivery system 12, coaxially disposed around the guidewire 7. The filter deployment and delivery system 12 comprises an outer member 13 and an inner member 15, with the outer member 13 coaxially disposed around the inner member 15, and the inner member 15 coaxially disposed around the guidewire 7. The inner member 15 comprises a filter 1, removably attached near the distal end of the inner member 15. The filter 1 is collapsed into and constrained by the distal end of the outer member 13.

Figure 2:
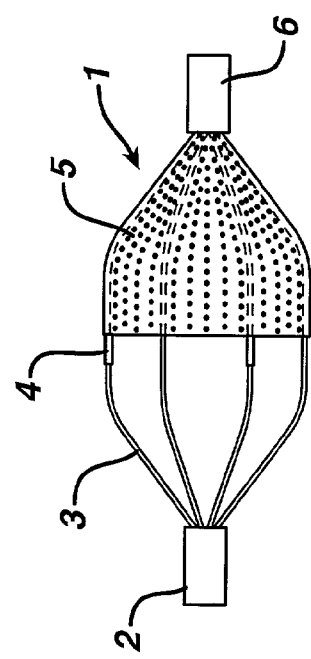
FIG. 2 illustrates an enlarged, partial, cross-sectional view of an exemplary embodiment of the filter of the low profile vascular filter system, with the filter in the open position, in accordance with the present invention.

As illustrated in FIG. 2, the filter 1, in the exemplary embodiment, comprises a proximal basket sleeve 2 and a distal basket sleeve 6, and a plurality of struts 3 therebetween to form a filter membrane support structure. The filter 1 further comprises at least one marker 4 attached to at least one strut 3. The filter 1 further comprises a permeable filter membrane 5 attached near the distal basket sleeve 6 and attached to the plurality of struts 3, as illustrated in FIG. 2. The filter 1 has a smaller first diameter for delivery, as illustrated in FIG. 1, and a larger second diameter for deployment, as illustrated in FIG. 2.

As illustrated in FIG. 3, the low profile vascular filter system in this exemplary embodiment comprises a guidewire 7, having a floppy tip 11, a distal marker 10 and a proximal marker 9. These markers 10, 9 serve two purposes. First, the markers 10, 9 identify the future location of the filter 1, under fluoroscopy, after the guidewire 7, without the filter 1, is inserted into the lumen. Secondly, as illustrated in FIG. 4, the distal marker 10 serves as a stop for the distal basket sleeve 6 after the filter has been positioned onto the guidewire 7. The distal basket sleeve 6 has a diameter greater than the maximum diameter of the proximal marker 9, but not greater than the maximum diameter of the distal marker 10. The proximal basket sleeve 2 has a diameter that is not greater than the maximum diameter of the proximal marker 9. Accordingly, the filter may be positioned between the distal marker 10 and the proximal marker 9, as illustrated in FIG. 4.

Figure 5:
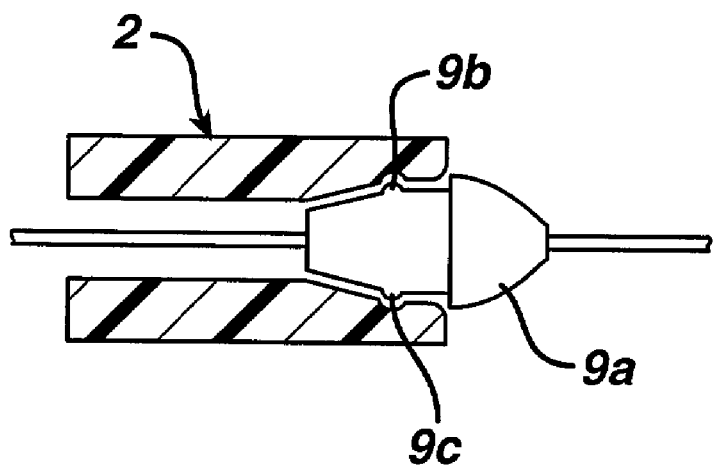
FIG. 5 illustrates an enlarged, partial, simplified, cross-sectional view of an exemplary embodiment of the proximal basket sleeve and proximal marker of the low profile vascular filter system, in accordance with the present invention.

FIG. 5 illustrates another exemplary embodiment of the present invention, wherein the proximal basket sleeve 2 and a modified proximal marker 9a lock together to minimize longitudinal movement of the device, while still allowing rotational movement of the device. The modified proximal marker 9a comprises a protruding ridge 9b which is engaged by an indentation 9c within the proximal basket sleeve 2. This may minimize movement of the filter 1 within the lumen, thereby avoiding potential vessel damage and/or accidental release of embolic particulates.

Figure 6:
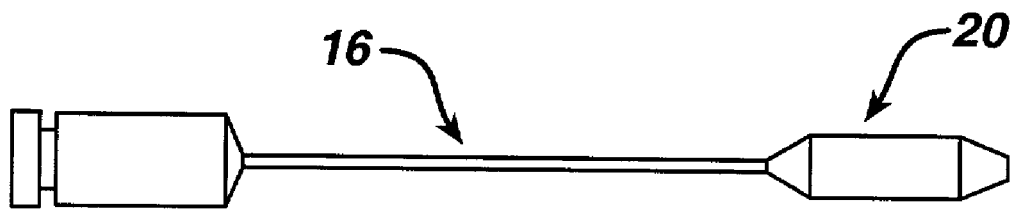
FIG. 6 illustrates an enlarged, partial, cross-sectional view of an exemplary embodiment of the retrieval catheter of the low profile vascular filter system, in accordance with the present invention.

As illustrated in FIG. 6, the exemplary embodiment of the present invention further comprises a retrieval catheter 16. The retrieval catheter 16 is coaxially disposable around the guidewire 7 (FIG. 1). The distal end 20 of the retrieval catheter 16 has a larger diameter than the body of the retrieval catheter 16. The distal end 20 of the retrieval catheter 16 may be inserted over the filter 1 (FIG. 1) to capture and collapse the filter 1, and to remove the filter 1 from the lumen.

As illustrated in FIGS. 1, 2, 3, 4 and 6, the low profile vascular filter system may be used to introduce a low profile guidewire into the lumen of a vessel, followed by delivery and deployment of a filter to capture embolic particulates released during the procedure. The guidewire and/or filter may then be retrieved and removed from the lumen. The guidewire 7, as illustrated in FIG. 3, may be introduced into the lumen of a vessel through femoral access. The guidewire 7, with a floppy tip 11, is positioned past an occlusion in a vessel, with distal marker 10 and proximal marker 9 identifying the future position of the filter under fluoroscopy. Then, as illustrated in FIG. 1, the filter deployment and delivery system may be introduced over the guidewire 7 and advanced through the lumen of the vessel. The filter 1 is removably attached near the distal end of the inner member 15, and the filter 1 assumes a smaller first diameter when collapsed and constrained within the distal end of the outer member 13. As illustrated in FIG. 4, the distal basket sleeve 10 is advanced over the proximal marker 9, but not the distal marker 10. In the exemplary embodiment, the distal marker 10 serves as a stop to prevent the filter 1 from advancing distally. The filter 1 is now in position between proximal marker 9 and distal marker 10, and the outer member 13 may be retracted to allow the filter 1 to achieve its larger second diameter. The inner member 15 may also be retracted, and the filter 1 remains in position on the guidewire. At this point, additional interventional devices, such as balloon catheters and stent delivery systems, may be advanced over the guidewire to complete the interventional procedure. The filter remains in position capturing embolic particulates. Then, the retrieval catheter 16, as illustrated in FIG. 6, may be advanced over the guidewire 7 to collapse and retrieve the filter 1. If the filter 1 has become filled with embolic particulates, and the procedure is incomplete, the retrieval catheter may retrieve filter 1 only, and allow the guidewire 7 to remain in position for the balance of the procedure.

The guidewire 7 may be made from any number of suitable materials, and may preferably be made from stainless steel or Nickel-Titanium alloy. The filter struts 3 may be made from any number of suitable materials, and are preferably made from Nickel-Titanium alloy. The filter markers 4 may be made from any number of suitable materials, and are preferably made from a radiopaque material such as gold, platinum, tantalum, niobium, molybdenum, rhodium, palladium, silver, hafnium, tungsten or iridium. The proximal marker 9 and the distal marker 10 on the guidewire 7 may be made from any number of suitable materials, and are preferably made from radiopaque materials such as gold, platinum, tantalum, niobium, molybdenum, rhodium, palladium, silver, hafnium, tungsten or iridium. The proximal basket sleeve 2 and the distal basket sleeve 6 on the filter 1 may be made from any number of suitable materials, and are preferably made from radiopaque materials such as gold, platinum, tantalum, niobium, molybdenum, rhodium, palladium, silver, hafnium, tungsten or iridium. The filter 1 may also comprise coatings or any other suitable means for enhancing the radiopacity of the device. The permeable filter membrane 5 may be made from any number of suitable materials, and is preferably made from a flexible polymeric material with elastomeric properties including, polyurethane, polyethylene or a co-polymer thereof, as well as combinations thereof. The permeable filter membrane 5 may comprise any number and configuration of openings/holes and preferably comprises openings/holes wherein the hole size is from about twenty to about three hundred microns in diameter. The openings/holes may be created by any suitable means, and may preferably be created by laser drilling. In alternate embodiments, the filter membrane 5 may comprise a porous material rather than manufactured openings/holes. The outer member 13 and the retrieval catheter 16 may be made from any number of suitable materials, and are preferably made from a polymeric material. The inner member 15 may be made from any number of suitable materials, and is preferably made from a polymeric or metallic material. The filter 1 may be removably attached to the inner member 15 by any suitable means, and may preferably be attached via a friction fit or a releasable latch. The permeable filter membrane 5 may be attached to the struts 3 by any suitable means, and may preferably be attached by a bonding or welding process. The struts 3 may be attached to the basket sleeves 2, 6 by any suitable means, and may preferably be attached by a bonding or welding process. The filter markers 4 may be attached to the struts by any suitable means, and are preferably attached to the struts by a bonding or welding process. The guidewire distal marker 10 and the guidewire proximal marker 9 may be attached to the guidewire by any suitable means, and are preferably attached to the guidewire by a bonding or welding process.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A vascular filter system comprising:
   a) a guidewire having a predetermined diameter, a proximal end, a distal end, a proximal marker having a first diameter and a distal marker having a second diameter, the proximal and distal markers being attached to the distal end of the guidewire;
   b) a filter deployment and delivery system including an inner member having a proximal end, a distal end, an inner diameter and an outer diameter, and an outer member having a proximal end, a distal end, an inner diameter and an outer diameter, the inner member being coaxially disposable around the guidewire and the outer member being coaxially disposable around the inner member;
   c) a filter removably attached to the distal end of the inner member, the filter including a filter membrane support structure having a proximal portion and a distal portion, a permeable filter membrane attached to the distal portion of the filter membrane support structure, a proximal basket sleeve connected to the proximal portion of the filter membrane support structure, the proximal basket sleeve having a diameter less than or equal to the first diameter of the proximal marker, and a distal basket sleeve connected to the distal portion of the filter membrane support structure having a diameter greater than the first diameter of the proximal marker and less than or equal to the second diameter of the distal marker such that the distal basket sleeve passes over the proximal marker and is stopped at the distal marker, the proximal basket sleeve further comprising a tapered end having a circumferentially oriented indentation and the proximal marker comprising a tapered section and a protruding ridge operatively associated with the indentation thereby allowing rotational movement and limiting longitudinal movement therebetween, the filter having a diameter for insertion and a diameter for deployment; and
   d) a retrieval catheter having a proximal end, a distal end, an inner diameter and an outer diameter, the retrieval catheter being coaxially disposable around the guidewire and the filter.

2. The vascular filter system according to claim 1, wherein the guidewire comprises a Nickel-Titanium alloy.

3. The vascular filter system according to claim 1, wherein the guidewire further comprises a floppy tip connected to the distal end of the guidewire.

4. The vascular filter system according to claim 1, wherein the proximal and distal markers comprise radiopaque material.

5. The vascular filter system according to claim 1, wherein the inner and outer diameter of the outer member of the filter deployment and delivery system is larger at its distal end to accommodate the filter.

6. The vascular filter system according to claim 1, wherein the filter membrane support structure comprises a plurality of struts connected to the proximal and distal basket sleeves.

7. The vascular filter system according to claim 6, wherein the plurality of struts comprise Nickel-Titanium alloy.

8. The vascular filter system according to claim 6, wherein the filter further comprises at least one marker band attached to at least one strut.

9. The vascular filter system according to claim 8, wherein the at least one marker band comprises radiopaque material.

10. The vascular filter system according to claim 1, wherein the permeable filter membrane comprises a flexible polymeric material.

11. The vascular filter system according to claim 10, wherein the permeable filter membrane comprises openings with diameters ranging-from twenty to three hundred microns.

12. The vascular filter system according to claim 1, wherein the proximal and distal basket sleeves comprise radiopaque material.

13. The vascular filter system according to claim 1, wherein the filter delivery and deployment system and the retrieval catheter are over-the-wire systems.

14. The vascular filter system according to claim 1, wherein the filter deployment and delivery system and the retrieval catheter are rapid exchange systems.

15. The vascular filter system according to claim 1, wherein the outer diameter of the retrieval catheter is larger at its distal end.

16. The vascular filter system according to claim 1, wherein the retrieval catheter further comprises means to retrieve the filter from the guidewire while the guidewire remains in position within the vasculature.

* * * * *